(12) United States Patent
Wetling (10) Patent No.: US 9,956,424 B2
(45) Date of Patent: May 1, 2018

(54) IONIZED GAS FOR MEDICAL TREATMENT

(75) Inventor: John Wetling, Hundested (DK)

(73) Assignee: WETLING IP TWIG LTD, Tortola (VG)

(*) Notice: Subject to any disclaimer, the term of this patent is extended or adjusted under 35 U.S.C. 154(b) by 674 days.

(21) Appl. No.: 12/991,716

(22) PCT Filed: May 7, 2009

(86) PCT No.: PCT/EP2009/055520
§ 371 (c)(1),
(2), (4) Date: Jan. 20, 2011

(87) PCT Pub. No.: WO2009/135896
PCT Pub. Date: Nov. 12, 2009

(65) Prior Publication Data
US 2011/0112522 A1   May 12, 2011

Related U.S. Application Data

(60) Provisional application No. 61/071,641, filed on May 9, 2008.

(30) Foreign Application Priority Data

May 9, 2008   (EP) ...................................... 08155975

(51) Int. Cl.
*A61B 18/18* (2006.01)
*A61N 1/44* (2006.01)
(52) U.S. Cl.
CPC ....................................... *A61N 1/44* (2013.01)
(58) Field of Classification Search
CPC ........................................................ A61N 1/44

USPC ................................. 604/23–26, 290; 607/2
See application file for complete search history.

(56) References Cited

U.S. PATENT DOCUMENTS

| | | | | |
|---|---|---|---|---|
| 1,839,876 A | * | 1/1932 | Hartman | 422/186.18 |
| 4,019,510 A | * | 4/1977 | Ellis | 604/20 |
| 4,340,047 A | * | 7/1982 | Tapper et al. | 604/20 |
| 5,433,735 A | * | 7/1995 | Zanakis et al. | 607/50 |
| 2001/0034519 A1 | | 10/2001 | Goble et al. | |
| 2002/0065533 A1 | | 5/2002 | Weaver et al. | |
| 2004/0116918 A1 | | 6/2004 | Konesky | |
| 2005/0209660 A1 | | 9/2005 | James | |

(Continued)

FOREIGN PATENT DOCUMENTS

| | | |
|---|---|---|
| CA | 2094651 | 10/1994 |
| EP | 1810626 A2 | 7/2007 |
| WO | WO1998050110 | 11/1998 |

(Continued)

OTHER PUBLICATIONS

D.P. Jones et al. "Effect of long-term ionized air treatment on patients with bronchial asthma", THorax (1976), 31, 428.*

(Continued)

*Primary Examiner* — Mark W Bockelman
(74) *Attorney, Agent, or Firm* — Fox Rothschild LLP (57) ABSTRACT

The present invention relates to a method for treatment of a pathology-affected site in a subject, the method comprising providing said site with a net electrical charge for a period of time by subjecting the subject to a flux of ionized gas molecules whereby is provided an electrical current between said site and tissue outside said site.

21 Claims, 4 Drawing Sheets

(56) References Cited

U.S. PATENT DOCUMENTS

2005/0273047 A1  12/2005  Takhar et al.
2006/0198903 A1   9/2006  Storey et al.

FOREIGN PATENT DOCUMENTS

| WO | WO2006/077582 | A2 | 7/2006 |
| WO | WO2006116252 | A2 | 11/2006 |
| WO | WO2007042029 | A1 | 4/2007 |
| WO | WO2008/131407 | A1 | 10/2008 |

OTHER PUBLICATIONS

"DC electrical stimulation for chronic wound healing enhancement. Part 1 Clinical study and determination of electrical field distribution in the numerical wound model" Karba et al. Bioelectrochemistry and Bioenergetics 43 (1997) 265-270.*

Bogie K. M. et al., (2000) "Electrical stimulation for pressure sore prevention and wound healing", Assist. Technol. 12, 50-66. Abstract.

Reich J.D. et al., (1991) "The effect of electrical stimulation on the number of mast cells in healing wounds" J. Am. Acad. Dermatol. 25, 40-46.

Albert S.F. and Wong E. (1991) "Electrical stimulation of bone repair". Clin. Podiatr. Med. Surg. 8, 923-935.

Dunn et al., (1984) "Electrical stimulation in treatment of delayed union and nonunion of fractures and osteotomies". South. Med. J. 77, 1530-1534.

Masureik C. et al., (1977) "Preliminary clinical evaluation of the effect of small electrical currents on the healing of jaw fractures". Clin. Orthop. 84-91.

Kahanovitz, Neil, US Musculosceletal review 2007, pp. 36-38.

Fujita M, et al., (1992) "The effect of constant direct electrical current on intrinsic healing in the flexor tendon in vitro. An ultrastructural study of differing attitudes in epitenon cells and tenocytes", J. Hand Surg. [Br.] 17, 94-98.

"Wireless Micro Current Stimulation (WMCS)—Accelerated Healing of Acute and Chronic Wounds", Case Studies Asia, Jun. 2015.

Kambouris et al: "Wireless electrostimulation: a new approach in combating infection?", Future Microbiology, Feb. 2017.

Ramadhinara and Poulas: "Use of Wireless Microcurrent Stimulation for the Treatment of Diabetes-Related Wounds: 2 Case Reports", Advances in Skin & Wound Care, Jan. 2013. pp. 1-4.

Marlise B et al.: "Use of a new method of Electrostimulation for hard-to-heal wounds",Spitalstsag. Abstract from a poster session as presented at the EWMA congress 2012 in Vienna. Spital STS AG, Thun, Schwiez.

Limbourg A et al.: "Wireless Microcurrent Stimulation (WMCS) of burns—influence on perfusion, epithelialization and germination", Meeting Abstract 35th Anniversary of the German-speaking Working Community on Combustion Treatment (DAV 2017). Chur, Switzerland. Jan. 18, 2017.

https://clinicaltrials.gov/ct2/show/NCT02712580.

* cited by examiner

IONIZED GAS FOR MEDICAL TREATMENT

CROSS-REFERENCE TO RELATED APPLICATIONS

This application is a §371 national stage entry of International Application No. PCT/EP2009/055520, filed May 7, 2009, which claims priority to European Patent Application No. 08155975.9, filed May 9, 2008, and U.S. Provisional Application No. 61/071,641, filed May 9, 2008,

FIELD OF THE INVENTION

The present invention relates to the field of electrotherapy. In particular, the present invention relates to electrotherapy of localized pathological areas or zones by means of treatment with ionized gas molecules such as ionized air molecules.

BACKGROUND OF THE INVENTION

Electrical stimulation (also termed electrostimulation or ES) is a well-known technology, which has been used in treatment of a large number of pathologies—when used in disease treatment, ES is often termed electrotherapy.

In practice ES involves the transfer of electric current through an applied surface electrode pad that is in electrolytic contact with the external skin surface and the area to receive the effect. In ES, at least two electrodes (a lead and a discharge electrode) are required to complete the electric circuit.

Using electrodes when ES treating a human or an animal includes the drawbacks that it is difficult i.a. due to manipulation of the electrodes, that the dosage is difficult to control (i.e. "administration" is a problem), and that it is known to be painful for the patients. In certain modes of ES (e.g. when using ES in wound treatment), there is also the added risk of infection because ES in such a context is an invasive method.

Despite this the literature on the ES has been increasing exponentially in recent years. About 95 percent are positive reports despite an extraordinarily wide selection of experimental techniques and models. Fourteen research groups report that electrical currents stimulated fracture healing with few if any complications in a total of 595 patients. The mechanisms of action and ideal technique for applying stimulation has yet to be determined Nevertheless, ES has been used as a therapeutic means in a number of conditions, notably in the treatment of various types of wounds, such as acute wounds, burns, chronic wounds including pressure ulcers, diabetic ulcers, venous ulcers, and arterial ulcers. In the section dealing with the detailed aspects of the present invention is included a review of a number of the practical uses of ES.

OBJECT OF THE INVENTION

It is an object of the present invention to provide improved means for effecting electrotherapy in order to overcome the above-mentioned drawbacks.

SUMMARY OF THE INVENTION

It has been found by the present inventors that a variant of ES, where charge is delivered by means of electrically charged gas molecules, provides for the same advantages as does traditional ES, but has the added advantages of not causing pain, being easy to administer and not involving any notable risks of contamination. Hence ES caused by transfer of ionized gas molecules such as negatively charged Oxygen or positively charged Nitrogen molecules provides an attractive alternative to traditional electrotherapy.

Hence, in its first and broadest aspect, the present invention relates to a method for treatment of a pathology-affected site in a subject, the method comprising providing said site with a net electrical charge for a period of time by subjecting the subject to a flux of ionized gas molecules whereby is provided an electrical current between said site and tissue outside said site.

In a second aspect, the invention relates to a method for treatment a subject suffering from asthma or other disease characterized by a pathology involving histamine release by mast cells or basophilic granulocytes, said method comprising subjecting the subject to a flux of ionized gas molecules for a period of time, said ionized gas molecules having a net positive or negative charge.

A third aspect relates to the medical use of ionized gas molecules in the two methods which constitute the $1^{st}$ and $2^{nd}$ aspects of the invention, i.a. the invention relates to ionized gas molecules for use in the therapeutic methods disclosed herein.

WO 2007/042029 discloses an air-ion transmitting device which comprises an ion generator for generating a dose of air-ions, a radiation emitting element for generating a dose of electromagnetic radiation, and a feedback structure which is adapted to determine an electrical current through a living object. It is also disclosed to use the air-ion transmitting device in treatment, where a current is passed through a portion of the living object body. WO 2007/042029 teaches improvement in general well-being and reduction of pain but there is no disclosure of localised ES in order to treat a local pathology.

CA 2,094,651 relates to an apparatus which is said to be is capable of delivering ionized gas to an area on a patient. However, the ionized gas constitutes a mixture of positively and negatively charged gas molecules and it does not appear that a net charge is transferred to the patient. Further, from the disclosure in CA 2,094,651 it is clear that the subject treated with the apparatus must be completely isolated from any electrical conductors.

DETAILED DISCLOSURE OF THE INVENTION

Legends to the Figures

DEFINITIONS

The expression "a pathology-affected site" is intended to mean an area or 3D shapes or structure on or in a living body in an animal, typically in a human being, where the effects of a pathological process can be observed. In this context, "pathology" should be construed broadly as any condition which causes discomfort or endangers the life of the animal in question.

Providing a "net electrical charge" means that a sufficient amount of electrical charge is provided to a pathology-affected site, whereby an electric current passes from said site to surrounding tissue for an appreciable period of time. This means that a current has to be established for at least 10 seconds, but often longer as detailed below. It should be emphasized that the electric current, which passes from the pathology-affected site to the surrounding tissue cannot be established precisely—when discussing this electrical current in quantitative terms in the present application, the quantity (measured in Ampere) is the one which may be measured in discharge electrode(s) which returns current from the subject to be treated to the device that delivers the ionized gas molecules.

"Ionized gas molecules" broadly refers to gas molecules which carry a net electrical charge. Typical examples are negatively charged oxygen molecules ($O_2^-$) and positively charged Nitrogen molecules ($N_2^+$) because of the abundancy of oxygen and nitrogen in atmospheric air, but any gas molecule capable of carrying a net charge is useful in the practice of the present invention, as long as such ionized molecules do not provide unacceptable adverse or toxic effects on the subjects treated.

A "discharge electrode" is an electrode attached to a treated subject which ensures that the net charge provided by the ionized gas molecules do not simply build up a static charge in the subject but instead establishes an electrical current which passes through the subject to the discharge electrode. Typically, such an electrode will be in the form of a strap, but any convenient physical form may be useful. A special example of a discharge electrode is a "return electrode", which is connected (optionally via a control unit) to the device which supplies the ionized gas ions—this enables that a return current may be measured and this in turn enables full control over the current sent through the treated subject as a consequence of the delivery of the ionized gas molecules.

A "gas ion transmitting device" is a device or apparatus, which is capable of generating a stream, jet or flux of ionized gas molecules having a net electrical charge and where the direction of the stream, jet or flux may optionally be controlled with respect to dosage, intensity and direction. Specifics concerning such devices are discussed below.

PREFERRED EMBODIMENTS

General Considerations for all Aspects of the Invention

As mentioned above, ES has previously been utilised therapeutically in a number of conditions and been demonstrated to provide advantageous effects. Further, as will appear from the examples, the present invention has been successfully used in the treatment of persistent wounds, burns and other wounds notoriously exhibiting a low healing-rate. This underscores that treatment with ionized gas molecules as an alternative to electrodes in order to deliver an electric current in a wound is effective and also involves several advantages, since it is virtually painless for the patient, is easy to administer, and provides a low risk of contamination. Further, knowing from the prior art that traditional ES has been utilised successfully for treatment, amelioration and prophylaxis of a number of conditions, the present inventors have concluded that delivery of ionized gas molecules according to the teachings herein will be an advantageous alternative for treatment, amelioration and prophylaxis of exactly the same types of conditions.

The practical implementation of the inventive method entails that the subject to be treated is exposed for a period of time to a stream or jet (or flux) of ionized gas molecules which carry a net charge sufficient to generate a current in the subject. The stance and position of the subject to be treated is inessential and will be chosen as a matter of practicality and convenience; often the subject will be resting on a bed or a treatment bench, but also a standing or sitting position is possible, depending on the exact condition to be treated.

The ionized gas molecules (also termed "air ions") are conveniently provided from a gas ion transmitting device which includes gas ion generator (also known as an "air ionizer"). This type of device is known to the skilled person and is e.g. used in the semiconductor industry to counteract electrostatic charge building when handling and transporting microchips and wafers. However, a suitable gas ion transmitting device for use in the present invention is one which, apart from generating the ions, is capable of delivering a directed stream of gas ions having either a predominant positive or a predominant negative charge (where e.g. the devices used in the semiconductor industry typically deliver a balanced mixture of positive and negative ions). In brief, such an apparatus generates a high voltage applied to an electrode, which thus produces an electrical field that is most intense in a defined region (e.g. immediately adjacent a sharply pointed tip). The intense electrical field disrupts the normal charge state of molecules of air gases (e.g. nitrogen and oxygen) in the region adjacent to the sharply pointed tip and some of the molecules become negative or positive ions, depending upon whether the molecule attains an excess or a deficiency of electrons (typically oxygen will become negatively charged, whereas nitrogen will become positively charged). The ions having a polarity opposite from the polarity of the high voltage of the electrode are attracted to the electrode and are neutralized, whereas ions of the same polarity as the high voltage electrode repelled by the electrode and are dispersed outwardly. The subsequent projection towards the treated subject of the thus generated air ions can be controlled by e.g. using blowers or fans; further the subject is connected to a return electrode of opposite polarity than the projected gas ions, and this normally ensures a correct projection of the ionized gas molecules in the desired direction towards the patient. Also, such a return electrode can be equipped with an amperemeter or other device for measuring the current passing through the electrode whereby the dosage of the ionized gas molecules can be controlled by a feed-back mechanism where gas ion generation and projection is controlled in response to the current passing through the electrode (i.e. if the return current exceeds a preselected current, the amount of gas ions projected by the ionized gas transmitting device is down-regulated, and vice versa).

Since the charge of the projected ionized gas molecules will depend on the polarity of the electrode, it is possible to generate DC of either polarity in the subject, and by shifting polarity of the electrode in the gas ion transmitting device during the treatment, it is possible to generate an AC based treatment, cf. below for details.

A suitable apparatus for delivering the ionized gas molecules is e.g. disclosed in WO 98/50110 and also WO 2007/042029 discloses a suitable apparatus, which also includes a further feature of providing electromagnetic radiation to the site of treatment.

Considerations and Embodiments in Relation to the First Aspect of the Invention

Typically (and conveniently) the ionized gas molecules used in the invention are derived from atmospheric air, but the practice of the present invention does not require this. Any acceptable ionized gas (supplied from a pressurized flask, e.g.) may find use in the present invention, as long as it can carry the necessary charges from the ionized gas transmitting device to the subject being treated.

Typically, the net electrical charge of the ionized gas is negative—first and foremost because it is fairly uncomplicated to generate ionized oxygen (which is negatively charged), whereas the generation of positively charged Nitrogen ions is energetically a less favourable process. So, preferably, the ionized gas molecules are negatively charged oxygen molecules.

However, it will be understood that the net electrical charge may also be positive and in that case the ionized gas molecules are typically positively charged Nitrogen molecules.

In order to ensure that an electric current is established between the pathology-affected site and surrounding tissue a discharge electrode is conveniently located outside said site on or in the subject's body so as to sustain the electrical current between said site and the discharge electrode. Said discharge electrode may, as indicated above, be a return electrode which establishes an electric circuit where charge is passing from the ionized gas transmitter device to the patient and where charge leaves the patient to the ionized gas transmitter devise, thus establishing a controllable circuit.

In some embodiments of the first aspect, the phase of the electrical current is kept substantially constant over time during treatment, i.e. the patient is subjected to a DC electrotherapy treatment. However, in other embodiments it may be convenient to shift the direction of the electrical current at least once during treatment by shifting the charge of the ionized gas molecules (typically while simultaneously shifting the polarity of the discharge electrode). It is contemplated to shift the direction of the electrical current several times during a treatment session, e.g. at intervals selected from about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 20 minutes, about 25 minutes, and about 30 minutes.

Typically, the flux of ionized gas molecules is projected directly onto the pathology-affected site or, alternatively onto the surface of the subject's body covering said site. The important goal to achieve is the provision of an electric current which passes from the pathology related site to surrounding tissue.

The ionized gas molecules are, as mentioned above, provided by means of a gas ion transmitting device. It is preferred that the electrical current obtained in the patient is at least 0.1 $\mu$A, such as at least 0.2, at least 0.3, at least 0.4, at least 0.5, at least 0.6, at least 0.7, at least 0.8, at least 0.9, at least 1.0, at least 1.1, at least 1.2, at least 1.3, at least 1.4, and at least 1.5 $\mu$A. It is further preferred that the electrical current is at most 100 $\mu$A, such as at most 50 $\mu$A, at most 40, at most 30 at most 20, at most 15, at most 10, at most 9, at most 8, at most 7, at most 6, at most 5, at most 4, at most 3, and at most 2 $\mu$A. In the practice of the invention good results have been obtained with an electric current of about 1.5 $\mu$A, but currents of about 0.5, about 0.6, about 0.7, about 0.8, about 0.9, about 1.0, about 1.1, about 1.2, about 1.3, about 1.6, about 1.7, about 1.8 about 1.9, about 2.0, about 2.2, about 2.4, about 2.6, about 2.8, about 3.0, about 3.2. about 3.5 and about 4.0 $\mu$A are all of relevance.

The treatment time for one treatment session is typically at least 1 minutes, but normally longer, such as at least 5, at least 10, at least 15, at least 20, at least 30, at least 40, at least 50, at least 60 minutes, at least 2 hours, at least 3 hours, at least 4 hours or even at least 6 hours. On the other hand, the treatment time is typically at most 24 hours, such as at most 12 hours, at most 5 hours, but may be lower, such as at most 4.5 hours, at most 4 hours, at most 3.5 hours, at most 3 hours, at most 2.5 hours, and at most 2 hours. It should be mentioned though, that treatment times for several days or weeks may be necessary when treating certain conditions such as aggressive cancers.

Typical treatment times are selected from about 20 minutes, about 30 minutes, about 40 minutes, about 50 minutes, about 55 minutes, about 60 minutes, 65 minutes, about 70 minutes, about 80 minutes, and about 90 minutes are all relevant.

Treatment sessions may be performed more than once, e.g. several times a day, but typically treatment is performed at regular intervals (e.g. daily) until a clinical end-point has been reached (e.g. the healing of injured tissue).

As mentioned above, the first embodiment of the invention relates to a method for treatment of a pathology-affected site in a subject, the method comprising providing said site with a net electrical charge for a period of time by subjecting the subject to a flux of ionized gas molecules whereby is provided an electrical current between said site and tissue outside said site.

This aspect of the invention therefore aims at ensuring that an electrical current flows between the pathology-affected site and "surrounding tissue".

Said pathology-affected site may be selected from the group consisting of a wound area (e.g. after trauma or surgery); injured tissue (e.g. after trauma or surgery) such as injured tendon and/or ligament tissue, injured peripheral or central nerves; a site exhibiting localized pain; a site exhibiting edema; a solid malignant tumour (e.g. carcinoma, adenocarcinoma, liposarcoma, fibrosarcoma, chondrosarcoma, osteosarcoma, leiomyosarcoma, rhabdomyosarcoma, glioma, neuroblastoma, medulloblastoma, malignant melanoma, malignant meningioma, neurofibrosarcoma, choriocarcinoma, malignant teratoma, and heamangiosarcoma of any tissue distribution and tissue location); and a localised non-solid malignant tumour (such as a myeloma).

The rationale behind the first aspect is the following: Treatment with ES, where the present invention can provide an attractive alternative, is described in a number of references, which primarily deal with use of ES as a therapeutic means which promotes healing of various types of injured tissue. Without being limited to any theory, it is believed that the electric current produced as a consequence of the present treatment assists in attracting cells which normally play a major role in inflammation and tissue repair.

Further, the present invention has been utilised successfully on human patients suffering from a variety of slow- or non-healing wounds, and since the wound healing process is not fundamentally different from e.g. healing of an internal injury, it is concluded that a large number of tissue injuries are relevant targets for the presently disclosed treatment method.

In the following is provided an overview of the existing ES therapies, where the present method of the first aspect of the invention is an attractive alternative to traditional ES:

Wound Treatment and ES

A review of the use of ES in wound treatment can be found in Bogie K. M., Reger S. I., Levine S. P., and Sahgal V. (2000) "Electrical stimulation for pressure sore prevention and wound healing". Assist. Technol. 12, 50-66. Abstract: This paper reviews applications of therapeutic electrical stimulation (ES) specific to wound healing and pressure sore prevention. It is reported that the application of ES for wound healing has been found to increase the rate of healing by more than 50%. Furthermore, the total number of wounds healed is also increased. It is also reported that optimal delivery techniques for ES therapy have not been established to date. A study of stimulation current effects on wound healing in a pig model has shown that direct current (DC) stimulation is most effective in wound area reduction and alternating current (AC) stimulation for wound volume reduction at current densities of 127 $\mu A/cm^2$ and 1,125 $\mu A/cm^2$, respectively. It is also reported that surface stimulation studies have shown that ES can produce positive short-term changes in tissue health variables such as regional blood flow and pressure distribution. The use of an implanted stimulation system consisting of intramuscular electrodes with percutaneous leads has been found to produce additional long-term changes, so it is suggested that an implantable ES system may have great potential for pressure sore prevention.

Reich J. D., Cazzaniga A. L., Mertz P. M., Kerdel F. A., and Eaglstein W. H. (1991) "The effect of electrical stimulation on the number of mast cells in healing wounds". J. Am. Acad. Dermatol. 25, 40-46. This reference reports the effect of ES on the numbers of mast cells in wounds and other cutaneous disorders, where ES has been shown to be effective in treating many of these disorders. In a pig model, highly significant reductions in the number of mast cells were seen in electro-stimulated animals when compared with nonstimulated control wounds. It was concluded that the ability of electrical stimulation to decrease the number of mast cells may be related to a reduction of either proliferation or migration of these cells and may prove to be a valuable therapeutic technique.

To conclude, the method of the invention is useful in treatment of wounds, especially slow-healing and non-healing wounds (cf. also the examples).

It is therefore a preferred embodiment of the first aspect of the invention to utilise the method on a wound area, such as a slowly healing or non-healing wound area. It is, as demonstrated in Example 2, thereby possible to facilitate healing of the wound. It is believed that especially good results are obtained when the net electrical charge carried by the ionized gas molecules establishes an electrical current between the surface of the wound area and underlying tissue.

Bone Repair and ES

Albert S. F. and Wong E. (1991) "Electrical stimulation of bone repair". Clin. Podiatr. Med. Surg. 8, 923-935. This reference reports that electrical stimulation demonstrates consistently high success rates in recalcitrant, complicated nonunionsa and speculates that that acceleration of fracture repair by electrical stimulation will become more widespread in the future.

Dunn A. W. and Rush G. A., III (1984) "Electrical stimulation in treatment of delayed union and nonunion of fractures and osteotomies". South. Med. J. 77, 1530-1534 reviews the cases of 52 patients with 52 ununited fractures and osteotomies who were treated with two methods of electrical stimulation, one surgical, the other nonsurgical. Seventeen patients, 14 of whom had concomitant bone grafting, had implantation of a bone growth stimulator. There were three synovial pseudarthroses but no active infection in this group. The overall success rate in healing of the fractures was 82%. Thirty-five patients, of whom four had initial concomitant bone grafting, were treated with pulsing electromagnetic fields (PEMF). There were six draining infections but no pseudarthrosis in this group. Two nonunions healed after bone grafting was combined with PEMF treatment, when the latter alone had failed. Eighty-one percent of the fractures united, and drainage ceased in five of the six infections.

Masureik C. and Eriksson C. (1977) "Preliminary clinical evaluation of the effect of small electrical currents on the healing of jaw fractures". Clin. Orthop. 84-91 reported the results of a clinical investigation of the effect of small electrical currents on the healing of mandibular fractures in 40 patients when compared to an equal number of controls with similar fractures. The repair process was enhanced in the electrically stimulated fractures compared to the controls in the first 10-14 days after reduction.

Finally, in US Musculosceletal review 2007, pages 36-38, Neil Kahanovitz presents a review of various ES techniques and their successful application as adjunctive therapy for the surgical methodology known as spinal fusion.

Hence, since traditional ES has proven effective in promoting bone repair, it is contemplated that the present invention will also be useful for this purpose.

Repair of Other Tissue

Fujita M., Hukuda S., and Doida Y. (1992) "The effect of constant direct electrical current on intrinsic healing in the flexor tendon in vitro. An ultrastructural study of differing attitudes in epitenon cells and tenocytes". J. Hand Surg. [Br.] 17, 94-98, investigated the effects of electrical stimulation upon the reparative processes in flexor tendons cultured in vitro. After one or two weeks of incubation, the unstimulated control tendons were covered with fibroblastic surface cells, thought to have originated from the epitenon. In contrast, the tendons subjected to electrical stimulation had no proliferation of the epitenon cells in the surface layer. The results indicate that electrical currents of low amperage suppress adhesion-causing synovial proliferation in the epitenon and promote active collagen synthesis in the tenocytes. This suggests the potential value of electrical stimulation in the control of adhesion formation after flexor tendon repair.

Hence, since traditional ES has proven effective in promoting tendon repair, it is contemplated that the present invention will also be useful for this purpose, but also more broadly for repair of any tissue (which has a capacity for healing) which has been injured in one way or another. Thus all types of tissue which has been injured by means of a trauma or otherwise (e.g. surgery) will be a suitable target for the presently disclosed method.

Hence, in post-operational settings (i.e. after surgery), the present invention will be applicable as adjunctive therapy. This is especially interesting, since the present method also shows promise in alleviating local pain. In post-surgery, the treatment will include the benefits of reduced need for sedatives and analgetics, a potential decrease in incidence of depression, earlier mobility, fewer instances of postoperative pulmonary complications, and, in some cases, a reduced length of stay in the Intensive Care Unite ICU. The patient will normally be treated in bed in a manner generally described above. The patient will be treated 45-60 minutes per day, typically over the area that causes the pain (i.e. the surgically traumatized area), and the patient will be treated daily until an acceptable result has been achieved.

The present invention is also believed to be effective in promoting healing of nerve injuries, both peripheral and possibly also central, thereby activating nerves that innervate extremities or other parts of the body affected by permanent or temporary paralysis. Such paralysis can e.g. be the result of a spinal cord injury, head injury, stroke or other neurologic disorders.

The patient will be treated as discussed generally above, where the ionized gas molecules will be delivered over the site of nerve injury, e.g. over the spinal cord or over the exact site of the nerve lesion. The patient will be treated daily until an acceptable result has been achieved.

Similarly, the present invention can also be used to promote recovery from orthopedic and neuromuscular diseases, where the motor cortex of the brain is restored or by stimulus at the periphery. The patient will in such a case be treated with a flux of ionized gas for 45-60 minutes e.g. over the spinal cord, at the back of the head or directly down in the head. The patient will be treated daily until an actable result has been achieved.

The present invention may also provide a localised pain treatment method, where ionized gas carrying a net positive or negative charge is projected over the painful site. The subject to be treated is positioned in an optimum manner as described above depending on the position and size of the site of pain and at least one discharge electrodes (normally using straps attached to the ankles or wrists) is located on the subject's body, remote from the site of pain in order to ensure that a net current will run through the site of pain. The method is applicable to all kinds of localized pain such as low back pain, myofascial and arthritic pain, neurogenic pain, and postsurgical pain. The patient will be treated 45-60 minutes directly on the spot for the pain and the treatment will normally be repeated daily until an acceptable result has been achieved.

Also various types of edema can be treated by means of the present invention, thereby reducing traumatic edema resulting from the disruption of blood vessels which often accompanies musculoskeletal injuries such as acute strains and sprains. The treatment will also facilitate the voluntary muscle pump activity which assists in lymphatic and venous drainage and thus aid in resolution of posttraumatic edema.

The patient will normally be treated in bed or on a treating bed in a manner as described above for 45-60 minutes over the edemic area. The patient will be treated daily until an actable result has been achieved.

Reduction of Drug Resistance in Cancer Cells

It has previously been demonstrated that ES facilitates the cellular uptake of cytostatic drugs (notably doxorubicin), whereby cells were killed even at low doxorubicin concentrations. Hence, ES may improve the efficacy of existing chemotherapeutic treatments when used as adjunctive therapy. Also in this setting the present invention may provide a safe and non-discomfort causing treatment regimen.

The patient can be treated in any convenient stance and position and have the discharge electrodes attached around angles and/or wrists. The patient will be treated 45-60 minutes, typically over the facial area, just prior to receiving chemotherapy.

Thus, the rationale behind the treatment of sites of malignant tumours is primarily the fact that ES in general will provide for an enhanced effect of anticancer chemotherapy.

Strokes caused by an embolus in the brain can also be ameliorated by means of the present invention. The goal of the treatment is to decrease the embolic site in a blood vessel and to increase the flow of oxygen-rich blood to the brain. Also ischemia may be treated in exactly the same way, the goal being essentially the same, namely to secure and/or reestablish blood-flow in an ischemic area.

The patient will be treated with the ionized gas for 45-60 minutes over the facial area and treated daily until an acceptable result has been achieved (the goal of the treatment is to restore the blood supply and to minimise the damage or dysfunction of tissue).

It is also believed that patients suffering from Parkinson's disease (and other neurodegenerative disorders such as Alzheimer's disease) will benefit from the present treatment. In essence, Parkinson's disease is caused by a progressive and specific loss of cells in the substancia nigra in the CNS. Since the present invention is useful in stimulating cells to maintain their activity and function (cf. the discussion of mast cells below), it is believed that the same effect may be attained from cells which are "struggling". The patient will be treated 45-60 minutes down in the face and will be treated daily until an acceptable result has been achieved.

Considerations and Embodiments in Relation to the 2$^{nd}$ Aspect of the Invention The second aspect of the invention relates to treatment of asthma and type I allergy, cf. above.

As shown in the example section, in vitro experiments demonstrate that histamine release from mast cells is sensitive to electrostimulation. Since asthma is one disease where histamine release by mast cells is an important pathological factor, the present invention may advantageously be used in treatment amelioration of asthma. Similarly, type I allergies where IgE mediated release of histamine from mast cells and basophilic granulocytes play a central role is also a relevant disease target for the treatment method of the current invention. It is therefore believed that transfer of charge using airborne, charged gas molecules to carry the charge to be released on the skin on a person suffering from asthma or type I allergy will help the patient to recover or will reduce the risk of later disease.

The goal of the treatment is to help restore or control mast cell function in people with asthma or type I allergy. The patient will normally be asked to rest on a treatment bed and will be connected to the return straps (the discharge electrodes) around the ankles or around the wrist in order to secure that the ionized gas stream will provide a current between the treated area and the straps. In each treatment, the patient will typically be treated with the ionized gas for 10-30 minutes on the anterior and on the posterior side of the torso, respectively, i.e. a total treatment time of between 20 and 60 minutes.

The patient will be treated daily until an acceptable result has been achieved.

In this second aspect of the invention, the flux of ionized gas molecules is preferably projected onto the thorax and/or the face of the subject, but for some patients, where this mode of treatment is too aggressive, it is necessary (and indeed possible) to treat other parts of the body remote from the respiratory system (e.g. hands or feet)

Otherwise, in this second aspect of the invention, the features described with respect to the choice of process parameters (insofar as these do not relate to the exact feature of ensuring a current from a defined pathology-affected site to surrounding tissue and does not relate to the pathologies discussed in the first aspect of the invention) apply mutatis mutandis to the second aspect of the invention. I.e. all choices of features used in the first aspect of the invention (such as the type and charge of gas molecules, the size and the polarity of the current established in the patient, the timing of the treatment, and the intervals between individual treatment sessions) are all equally applicable and useful when carrying out the second aspect of the invention.

Other Aspects of the Invention

It has been found that treatment of patients according to a variant of the first aspect (i.e. where it is secured that an electrical current passes through part of the body), it is possible to obtain appreciable improvements in the circulatory system, both locally and systemically. It is believed that this is the consequence in increase of metabolic demand in the treatment area. Patients are typically connected to the return wrist strap electrodes around the ankles or around the wrist and subsequently treated 45-60 minutes over the area to be treated. The patient has to be treated daily until an acceptable result has been achieved.

To conclude on this, it is also an aspect of the invention to apply the methods described generally herein for circulatory disorders, especially for improving blood circulation.

Example 1

Model Experiment Investigation Cellular Reactions to ES

Figure 1:
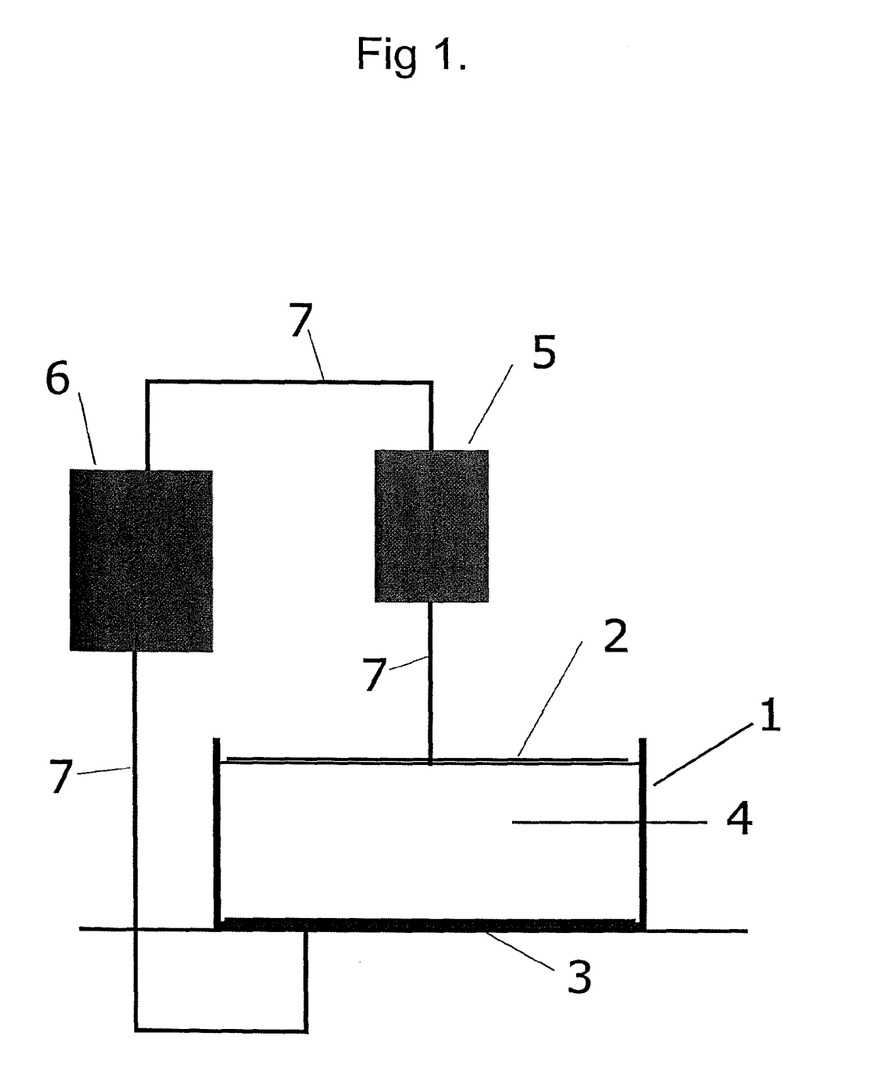
FIG. 1 shows in schematic form the experimental setup in Example 1.

The optimal laboratory set up system for investigation of the reaction on cells by the use of ES could be as shown in FIG. 1.

1 is a glass container, 2 is a top electrode which is cowering the total area to be receiving the current, 3 is a bottom electrode cowering the total area of the bottom, 4 is the target to be treated, 5 is a current generator, 6 is a control system, 7 denotes electrical cables.

The fluid in insulating container 1 is a cell suspension containing mast cells.

Mast cells and basophilic granulocytes are involved in anaphylaxis (which can ultimately lead to anaphylactic shock), where considerable amounts of heparin and histamine are deposited in the blood. These, and other biologically active substances present in the granules of the mast cells and basophilic granulocytes are to some extent responsible for the symptoms found with asthmatic and type I allergic reactions.

During an asthmatic or type I allergic attack, the mast cells are provoked to secrete histamine. By use of a chemically manufactured secretory substance, it is possible to simulate the process which takes place in the body when mast cells secrete histamine, and this makes it possible to investigate the relation between the mode of treatment and the production of histamine.

The investigation described below makes it possible to get an insight into the mechanisms, which, via exocytosis, leads to the secretion of mediators such as histamine.

Secretion of histamine is typically a result of an attack of asthma or allergy, and it causes various types of discomfort. Mast cells can be isolated, and have for many years successfully been used to investigate cellular changes taking place during the secretory process.

Glossary and Technical Concepts

Spontaneous histamine: The percentage of spontaneous histamine is a measure of the degree to which the cells used, now in the body fluid, have been affected during the process, or in other words, if the production of histamine is affected by the cell fluid in which the cells exist. If the spontaneous histamine is below 5%, the cells have not been affected to a measurable degree. If, on the other hand, the spontaneous histamine is above 5%, the cells are said to be stressed. The spontaneous histamine is thus a way of controlling that the cells used in the tests behave like normal, healthy cells.

Exocytosis: A process by which cells secrete certain substances. For instance, mast cells secrete histamine through exocytosis.

Cell Suspension: Cell Plus Extracellular Fluid.

Neutral conductor: The necessary earth wire to make sure that ion generators, measuring equipment and patients are grounded, in order to be able to interpret the currents measured.

Compound 48/80: During an allergic or asthmatic attack, mast cells are provoked to increase their production of histamine. Compound 48/80 is a synthetic inducer of the secretory process and thus of the secretion of histamine from mast cells. By adding different concentrations of compound 48/80 to the cell suspensions and thus provoking different rates of histamine secretion, it is possible to investigate to what extent ES may influence on the undesired secretion of histamine from the mast cells.

Using the set-up system as shown in FIG. 1, it is thus possible to measure the result of providing an electrical current between electrodes 2 and 3 through the mast cell containing liquid in container 1. The current will flow in essentially direct lines from the entire upper surface of the fluid to the bottom electrode 3.

With the first series of experiments, the fluid in the insulating container was a cell suspension containing mast cells. The purpose of these experiments was to determine if mast cells react to ES.

After a current had been sent through the suspension at a time interval varying from experiment to experiment, compound 48/80 was added in various concentrations, and the reactions of the mast cells in terms of histamine secretion were studied.

There was no doubt that the reaction of the mast cells depended on the current treatment, but the results were rather variable.

If, for instance, an experiment was repeated the following day with the same current intensity in the same time interval, the reaction of the mast cells was sometimes very different, and a positive reaction might even be replaced by an overreaction.

Such results are obviously not easy to interpret, but they suggest that the properties of the mast cells vary from time to time.

We now developed the theory that the treatment with ES directly on a fluid containing cells primarily is too powerful, and that the effect observed on the cells was caused by a subsequent interaction between the cell fluid and the cells.

In order to find out whether this was the case, a series of experiments was carried out with a cell fluid without mast cells.

With this treatment, currents of positive as well as negative were passed through the fluid samples for a period of one hour, using the set-up shown in FIG. 1. The same (numeric) current intensity was used for all experiments. After the exposure to current, mast cells were added to the samples treated as well as to untreated samples.

After a period of 30 minutes, compound 48/80 was added to concentrations of 0.1, 0.2 and 0.3 µg/ml.

Figure 2:
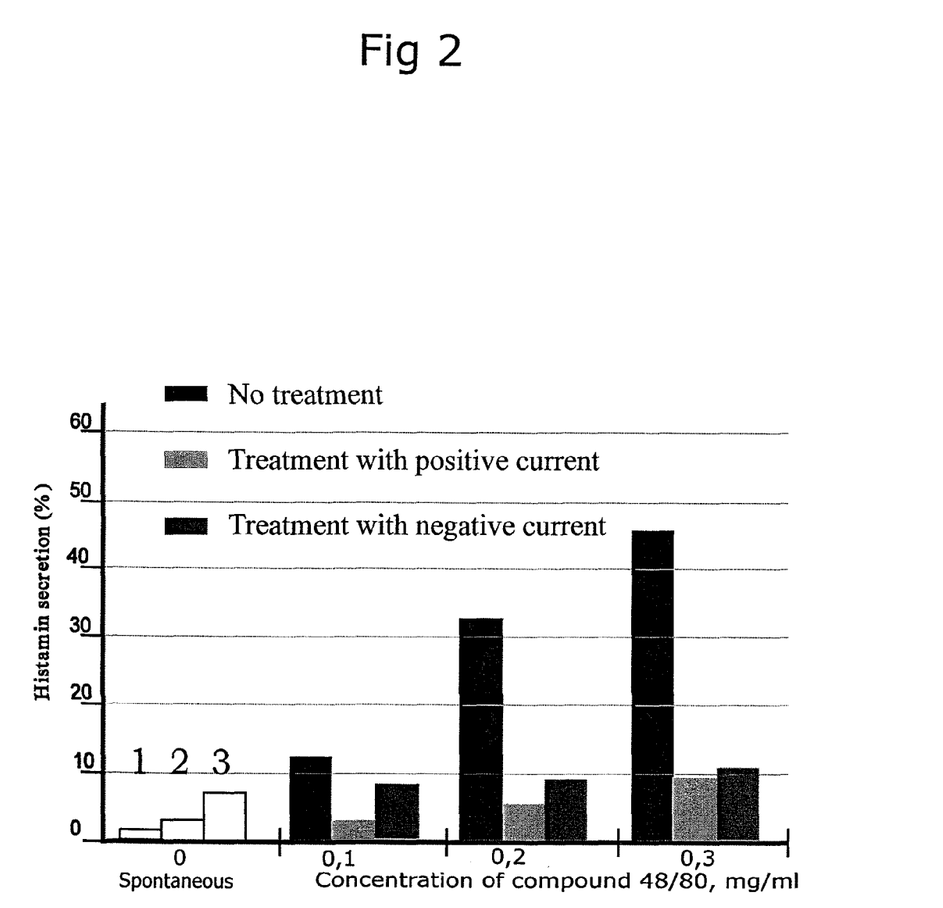
FIG. 2 shows a graph over the results from the experiments in Example 1.

The result is shown in the graph in FIG. 2.

The results show that the production of histamine increases dramatically with the concentration of compound 48/80, but also that it is possible to reduce the production of histamine considerably by treating the cell fluid with Electrical Stimulation but that it seems to be difficult to do it directly on a suspension containing cells, even by using a current at 1.5 µA.

Example 2

The Use of the Present Invention in Wound Healing
Rat Trial

A total number of 16 white healthy rats were each given a 20 mm×20 mm technical wound on the back. The rats were then separated randomly into two groups, a BLACK group and a RED group.

Each of the rats in group BLACK was given a black indication as a number from 1-8

Each of the rats in group RED was given a read indication as a number from 1-8.

Because all the rats were healthy, the healing time of the wounds were expected to be between 2 and 3 weeks.

The wounds were not covered or given any kind of saline.

By draw the BLACK group was elected to be treated with the treatment of the present invention for 45 minutes a day in 5 days. This was the only treatment this group received.

The RED group received no treatment at all.

| Rats group BLACK treated with the method of the invention (general findings) | | | | | | |
|---|---|---|---|---|---|---|
| Day 1 | 3 | 6 | 9 | 12 | 15 | 18 |
| Wound is dry. No reaction by touch. | Wound is dry and healing. No reaction by touch | Wound is healing. | Wound is healing fast. Size reduced 50% | Wound is healing fast. Size reduced 75% | Wound almost healed. | |

| Rats group RED with no treatment (general findings) | | | | | | |
|---|---|---|---|---|---|---|
| Day 1 | 3 | 6 | 9 | 12 | 15 | 18 |
| Wound is wet. Reaction by touch. | Wound is 50% dry and healing. No reaction by touch | Small part of wound is wet. Healing ongoing. | Wound is healing. Size reduced 30% | Wound is healing. Size reduced 50% | Wound healing. Size reduced 75% | Wound almost healed. |

Conclusion

The BLACK group treated according the invention exhibited a faster initiation of wound healing, and there was no reaction when touching the wounds already after day 1.

The wounds healed a few days faster than the RED group not being treated.

None of the rats being treated according to the invention exhibited any signs of adverse effects of the treatment.

Since all the rats were healthy and since the healing of the treated animals was faster it was concluded that the by using the method in non healing wounds could result in a much faster healing than seen by use of traditional ES. A number of human trials was hence set up.

Human Trials

ES is well known as a method in healing of non healing wounds, so the following treatments is all on patients suffering from non healing wounds, to show that the method is at least as useful as ES.

In a period over 14 months a total number of 45 patients have been treated with the method of the invention to verify the effect of the method. All patients were hospitalized by the beginning of the treatment, all suffering from serious wounds or burns, many of them with an generally critical condition.

All patients were informed about their situation and they all gave their informed consent to enter into the treatment of the invention.

Almost all patients were in severe pain and they required regular and strong analgesia.

All patients were treated by transferring 1.5 µA for 60 minutes in each treatment session (i.e. a total transfer of a net charge of 5.4 mC).

The treatment regimen was identical all patients. They were connected to a return cable by using wrist straps that was fixed to their ankles or their wrists.

The equipment were set to transfers 1.5 micro ampere and they all received the treatment 60 minutes a day 5 times a week.

24 patients were suffering from non healing lake wounds and in severe pain requiring strong analgesia.

4 of the 24 patients were dismissed from the surgical unit after 6-8 days of treatment. 15 patients recovered after a period of treatment of between 15-45 days, all being treated for 60 minutes 5 times a week.

Only 4 patients ended up being amputated, but recovered after 15-45 days at the hospital receiving the AMS treatment for 60 minutes 5 times a week.

1 patient past away due to other complications than the wounds.

All patients required significantly less analgesia.

11 patients were post operated suffering from non healing wounds and in severe pain requiring strong analgesia.

8 of those 11 patients did have the non healing wound on the abdomen. 2 of the patients past away due to other complications than the wounds. The remaining 6 patients recovered after 14-21 days of treatment according to the invention for 60 minutes 5 days a week.

2 of the 11 post operated patients had the non healing wound on the back, and they both recovered after just 5 days of 60 minutes treatment.

One of the 11 post operated patients had the non healing wound on the back and was suffering from an infection problem in the spinal cord as well. This patient recovered after only 3 days of treatment for 60 minutes per day. This patient recovered after only 3 days of treatment for 60 minutes per day.

All patients required significantly less analgesia.

5 patients were suffering from burns.

One of those 5 patients was in such a bad condition that the life was not to save.

The 4 patients suffering from $2^{nd}$ and $3^{rd}$ degrees burns were all discharged from the surgical unit mush faster than what was normal and the treatment of the invention seemed to include the further advantage of not leaving any significant scar tissue. All patients required significantly less analgesia.

5 patients were suffering from bed wounds.

One of those 5 patients past away because of other complications than the wounds.

One of the 4 patients was brought in to the surgical unit from another hospital suffering from a bed wound that had been operated without any good result.

This patient recovered after 10 days of treatment of the invention and was then discharged from the surgical unit to continue under normal wounds management.

The 3 of the 4 patients were treated according to the invention at the early beginning and after the first treatment the wound was dry and without pain. The treatment was repeated every $3^{rd}$ day for prevention.

All patients required significantly less analgesia.

The over all result shows that the treatment of the invention is useful as a means of ES therapy.

Example 3

Using Ionized Gas Molecules to Treat Mast Cells

Figure 3:
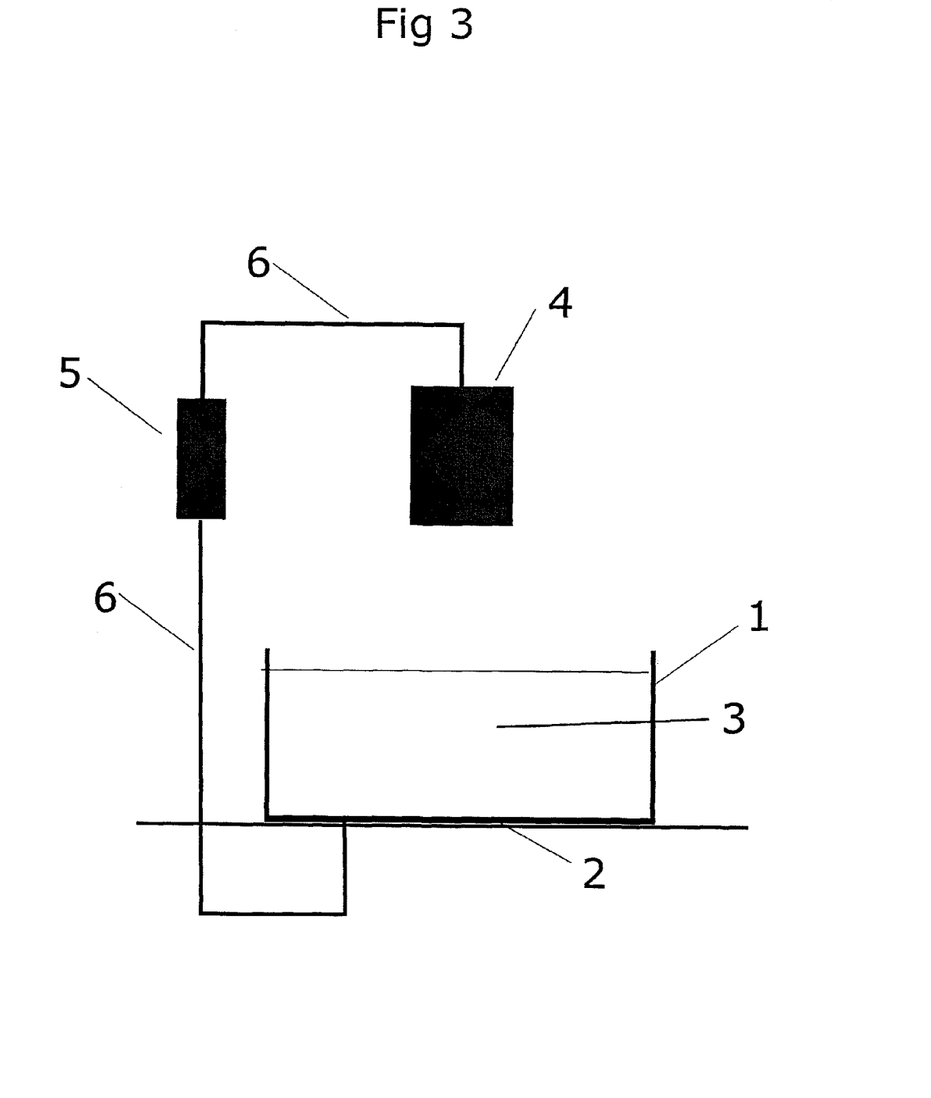
FIG. 3 shows in schematic form the experimental setup in Example 3.

A system for delivering ionized gas molecules to a mast cell suspension is shown in FIG. 3.

In this figure, 1 is a glass container, 2 bottom electrode, 3 is the target to be treated, 4 is the gas ion transmitting device, 6 is a control system, 7 are conducting cables.

With the first series of experiments, the fluid in the insulating container was a cell suspension containing mast cells.

The purpose of these experiments was to see if mast cells react to treatment with ionized gas molecules in analogy to Example 1.

Both $N_2^+$ and $O_2^-$ was dispensed over the suspension at a time interval varying from experiment to experiment, compound 48/80 was added to various concentrations, and the reactions of the mast cells in terms of histamine secretion were studied.

There was no doubt that the reaction of the mast cells depended on the current treatment, but the results were again rather variable.

If, for instance, an experiment was repeated the following day with the same current intensity in the same time interval, the reaction of the mast cells was sometimes very different, and a positive reaction might even be replaced by an overreaction.

Such results are obviously not easy to interpret, but they suggest that the properties of the mast cells vary from time to time.

We used our theory that the treatment with gas ions as well as the one with ES directly (as in Example 1) on a fluid containing cells primarily is too powerful, and that the effect observed on the cells was caused by a subsequent interaction between the cell fluid and the cells.

In order to find out whether this also was the case in this set-up system, a series of experiments was carried out with a cell fluid without mast cells.

With this treatment, currents of $N_2^+$ as well as $O_2^-$ were deliver to the fluid samples for a period of one hour, using the set-up shown in FIG. 3. The same (numeric) current intensity was used for all experiments. After the exposure to $N_2^+$ and $O_2^-$ current, mast cells were added to the samples treated as well as to untreated samples.

After a period of 30 minutes, compound 48/80 was added to concentrations of 0.1, 0.2 and 0.3 μg/ml.

Figure 4:
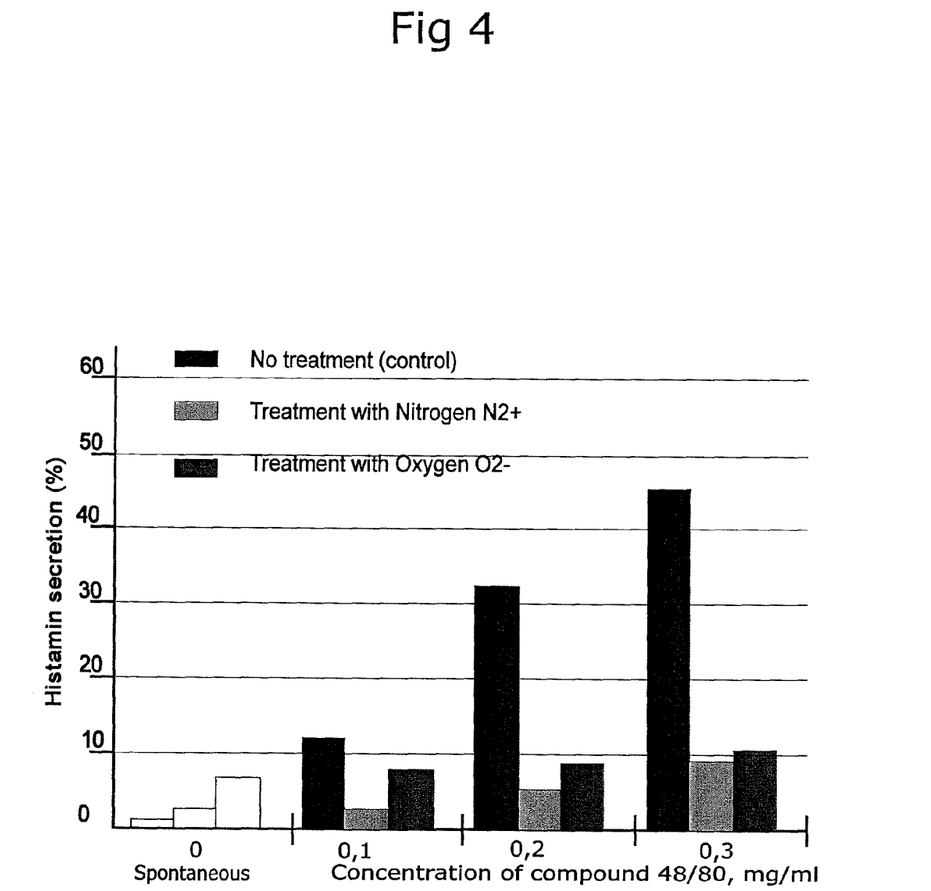
FIG. 4 shows a graph over the results from the experiments in Example 3.

The result is shown in the graph in FIG. 4.

The results show that the production of histamine increases dramatically with the concentration of compound 48/80, but also that it is possible to reduce the production of histamine considerably by treating the cell fluid with AMS technology.

Example 4

The Effect of on Asthma 22 children in the age between 4 and 13 (11 girls and 11 boys) were treated with gas ions according to the teachings herein for 5 days, each been given 10 minutes of treatment on the chest and 10 minutes of treatment on the back side of the thora at 1.5 μA.

All the children were under medical treatment using asthma medication.

The parents were informed in detail about the trial, and rapports about ES were shown to them to convince that there was no risk in using the method. A total explanation was been given about the technology of the present invention. Two couples of parents decided not to participate in the trial.

The parents was asked about the in-door climate at their homes, and it seems to be so that 3 of the children (2 girls and 1 boy) was from homes with in-door climate problems which could be the reason for their asthma.

The result was encouraging 14 of the children (9 girls and 5 boys) seems to be quit of their asthma and stopped using medication after the 5 days of treatment. 3 weeks later the 14 children continue being free of medication and further more 2 of those that did not end free of medication after the 5 days was in the week after the treatment less medicated than before.

The invention claimed is:

1. A method for treatment of a pathology-affected site in a subject, the method comprising providing said site with a net electrical charge for a period of time by subjecting the subject to a flux of ionized gas molecules whereby is provided an electrical current between said site and tissue outside said site,
    wherein
        a discharge electrode is located outside said site on or in the subject's body so as to sustain the electrical current between said site and the discharge electrode and wherein
        the electrical current has a direction, which is kept constant over time during treatment or wherein the direction of the electrical current is shifted at least once during treatment by shifting the charge of the ionized gas molecules,
        said site is a wound area, and wherein
        the electrical current is effective to increase wound healing rate.

2. The method according to claim 1, wherein said wound area is a slowly healing or non-healing wound area.

3. The method according to claim 2, wherein healing of the wound area is facilitated by said treatment.

4. The method according to claim 1, wherein the net electrical charge establishes an electrical current between the surface of the wound area and underlying tissue.

5. The method according to claim 1, wherein said gas is derived from atmospheric air.

6. The method according to claim 1, wherein said net electrical charge is negative.

7. The method according to claim 1, wherein the ionized gas molecules are negatively charged oxygen molecules.

8. The method according to claim 1, wherein said net electrical charge is positive.

9. The method according to claim 8, wherein the ionized gas molecules are positively charged Nitrogen molecules.

10. The method according to claim 1, wherein the direction of the electrical current is kept substantially constant over time during treatment.

11. The method according to claim 1, wherein the direction of the electrical current is shifted at least once during treatment by shifting the charge of the ionized gas molecules.

12. The method according to claim 11, wherein the polarity of the discharge electrode is shifted substantially simultaneously with shifting the charge of the ionized gas molecules.

13. The method according to claim 1, wherein the flux of ionized gas molecules is projected directly onto said site or to the surface of the subject's body covering said site.

14. The method according to claim 1, wherein the ionized gas molecules are provided by means of a gas ion transmitting device.

15. The method according to claim 1, wherein the electrical current is at least 0.1 µA.

16. The method according to claim 1, wherein the electrical current is at most 100 µA.

17. The method according to claim 1, wherein the treatment time is at least 1 minute.

18. The method according to claim 1, wherein the treatment time is at most 24 hours.

19. The method according to claim 1, wherein dosage of said ionized gas is controlled in response to electric current passing through said discharge electrode.

20. A method for treatment of a pathology-affected site in a subject, the method comprising providing said site with a net electrical charge for a period of time by subjecting the subject to a flux of ionized gas molecules whereby is provided an electrical current between said site and tissue outside said site, wherein
- a discharge electrode is located outside said site on or in the subject's body so as to sustain the electrical current between said site and the discharge electrode and
- the electrical current has a direction, which is kept constant over time during treatment or wherein the direction of the electrical current is shifted at least once during treatment by shifting the charge of the ionized gas molecules, and
- said site is a wound area, and
- said electrical current is at most 4 µA and effective to increase wound healing rate.

21. A method for treatment of a pathology-affected site in a subject, the method comprising providing said site with a net electrical charge for a period of time by subjecting the subject to a flux of ionized gas molecules whereby is provided an electrical current between said site and tissue outside said site, wherein
- a discharge electrode is located outside said site on or in the subject's body so as to sustain the electrical current between said site and the discharge electrode and
- the electrical current has a direction, which is kept constant over time during treatment or wherein the direction of the electrical current is shifted at least once during treatment by shifting the charge of the ionized gas molecules, and
- said site is selected from the group consisting of: a chronic wound and a burn, and
- said electrical current is at most 4 µA and effective to increase wound healing rate.

* * * * *